United States Patent
Oskin et al.

(10) Patent No.: US 9,949,627 B2
(45) Date of Patent: Apr. 24, 2018

(54) MEDICAL SYSTEM AND RELATED METHODS FOR DIAGNOSIS AND TREATMENT

(71) Applicant: Boston Scientific Scimed, Inc., Maple Grove, MN (US)

(72) Inventors: Christopher L. Oskin, Grafton, MA (US); Sujat Sukthankar, Shrewsbury, MA (US); Brian C. MacLean, Westford, MA (US); Roy Bromander, Salem, NH (US); Thomas M. Zappia, West Boylston, MA (US); Steven A. Olivieri, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 355 days.

(21) Appl. No.: 14/678,255

(22) Filed: Apr. 3, 2015

(65) Prior Publication Data
US 2015/0282701 A1    Oct. 8, 2015

Related U.S. Application Data

(60) Provisional application No. 61/975,489, filed on Apr. 4, 2014.

(51) Int. Cl.
*A61B 1/12* (2006.01)
*A61B 1/307* (2006.01)
(Continued)

(52) U.S. Cl.
CPC .......... *A61B 1/128* (2013.01); *A61B 1/00066* (2013.01); *A61B 1/0669* (2013.01); *A61B 1/07* (2013.01); *A61B 1/307* (2013.01)

(58) Field of Classification Search
CPC ..... A61B 1/00066; A61B 1/0669; A61B 1/07; A61B 1/12; A61B 1/128; A61B 1/307
(Continued)

(56) References Cited

U.S. PATENT DOCUMENTS

| 4,580,551 A | 4/1986 | Siegmund et al. |
| 4,753,222 A | 6/1988 | Morishita |

(Continued)

FOREIGN PATENT DOCUMENTS

| EP | 1 462 069 A1 | 9/2004 |
| EP | 2428157 A1 | 3/2012 |
| WO | WO 99/35995 A1 | 7/1999 |

OTHER PUBLICATIONS

International Search Report and Written Opinion from International Application No. PCT/US2015/024233, dated Jun. 10, 2015 (8 pages).

*Primary Examiner* — Joshua E Rodden
(74) *Attorney, Agent, or Firm* — Bookoff McAndrews, PLLC (57) ABSTRACT

According to aspects of the present disclosure, a medical device may include a tubular member. The medical device may also include a handle assembly connected to the tubular member. The handle assembly may include a handle housing, and an illumination assembly. The illumination assembly may include an illumination unit housed within an interior of the handle housing. The illumination assembly may also include an illumination fiber operatively coupled to the illumination unit. The illumination unit may extend through the interior of the handle housing into an interior of the tubular member. The illumination unit may also include a heat sink coupled to the illumination unit. The heat sink may be configured to receive heat from the illumination unit, and dissipate the heat away from the illumination unit.

18 Claims, 4 Drawing Sheets

(51) Int. Cl.
*A61B 1/00* (2006.01)
*A61B 1/06* (2006.01)
*A61B 1/07* (2006.01)

(58) Field of Classification Search
USPC .................................................. 600/131
See application file for complete search history.

(56) References Cited

U.S. PATENT DOCUMENTS

| | | | |
|---|---|---|---|
| 7,922,650 B2 | 4/2011 | McWeeney et al. | |
| 7,959,558 B2 | 6/2011 | Ito et al. | |
| 8,075,478 B2 | 12/2011 | Campos | |
| 8,106,569 B2 * | 1/2012 | Gershaw | A61B 1/0684 313/46 |
| 8,128,557 B2 * | 3/2012 | Scholly | A61B 1/128 600/112 |
| 8,152,715 B2 * | 4/2012 | Root | A61B 1/00034 600/131 |
| 8,167,470 B2 * | 5/2012 | Krattiger | A61B 1/07 362/294 |
| 8,221,311 B2 | 7/2012 | Campos | |
| 8,317,680 B2 | 11/2012 | Sato | |
| 8,388,523 B2 * | 3/2013 | Vivenzio | A61B 1/00105 362/574 |
| 8,900,132 B2 * | 12/2014 | Ishigami | A61B 1/00039 600/112 |
| 2002/0151768 A1 | 10/2002 | Akiba | |
| 2003/0081430 A1 * | 5/2003 | Becker | A61C 19/004 362/573 |
| 2003/0142712 A1 * | 7/2003 | Ikeda | H01S 5/02415 372/36 |
| 2004/0054254 A1 | 3/2004 | Miyake | |
| 2006/0085969 A1 * | 4/2006 | Bennett | A61B 1/0011 29/600 |
| 2006/0171693 A1 * | 8/2006 | Todd | A61B 1/00029 396/17 |
| 2006/0173242 A1 * | 8/2006 | Navok | A61B 1/0011 600/133 |
| 2006/0173245 A1 * | 8/2006 | Todd | A61B 1/0653 600/178 |
| 2006/0183977 A1 * | 8/2006 | Ishigami | A61B 1/00177 600/179 |
| 2006/0252992 A1 | 11/2006 | Mitsumori | |
| 2007/0225567 A1 * | 9/2007 | Kobayashi | G02B 23/2461 600/178 |
| 2007/0232858 A1 | 10/2007 | Macnamara et al. | |
| 2008/0055924 A1 * | 3/2008 | Ehrhardt | A61B 1/0669 362/580 |
| 2010/0076266 A1 | 3/2010 | Boulais et al. | |
| 2010/0121147 A1 | 5/2010 | Oskin et al. | |
| 2010/0238278 A1 | 9/2010 | Rovegno | |
| 2011/0009694 A1 | 1/2011 | Schultz et al. | |
| 2011/0306834 A1 * | 12/2011 | Schrader | A61B 1/00066 600/112 |
| 2012/0002422 A1 * | 1/2012 | Lia | A61B 1/0661 362/294 |
| 2012/0130160 A1 | 5/2012 | Borrye | |
| 2012/0162401 A1 | 6/2012 | Melder et al. | |
| 2013/0190561 A1 | 7/2013 | Oskin et al. | |

* cited by examiner

MEDICAL SYSTEM AND RELATED METHODS FOR DIAGNOSIS AND TREATMENT

CROSS-REFERENCE TO RELATED APPLICATIONS

This application claims the benefit of priority from U.S. Provisional Application No. 61/975,489, filed on Apr. 4, 2014, which is incorporated by reference herein in its entirety.

TECHNICAL FIELD

Embodiments of the present disclosure relate to medical systems and related methods for diagnosis and treatment. The medical systems and related methods may be used for ureteroscopy.

BACKGROUND

One challenge in diagnosing and treating internal areas of a subject's body has been adequately visualizing those internal areas. Visualization may be difficult to achieve in minimally invasive procedures, where elongated instruments with small diameters may be navigated through openings, passageways, and cavities of a subject's body, to access internal areas therein. Those elongated small-diameter instruments may include, for example, catheters or endoscopes.

Ureteroscopy is a procedure that may be performed to diagnose and treat urinary tract diseases and ureteral strictures. A ureteroscope may be inserted retrograde through the urinary tract to allow diagnosis and treatment of the urinary tract under visualization. Some ureteroscopes may not be disposable, and so after each successive urological procedure, they may have to be cleaned and sterilized before the next use. This may delay successive procedures. Such ureteroscopes may also require extensive and expensive maintenance for proper operation. The time and resources consumed for cleaning, sterilizing, and maintaining ureteroscopes my result in escalated costs for ureteroscopic procedures, and other medical procedures that utilize similarly configured scopes.

Furthermore, some ureteroscopes may have to be used with specialized electronic equipment. The specialized electronic equipment may include components that may operate in conjunction with components of those ureteroscopes. Purchasing and maintaining the specialized electronic equipment may be costly. In some cases, the specialized electronic equipment may not operate properly unless paired with one type of ureteroscope. When that type of ureteroscope is not being used, the specialized electronic equipment may remain un-utilized. Moreover, multiple types or models of specialized electronic equipment may be required for multiple ureteroscopes. Further still, repairing, replacing, or updating the specialized electronic equipment or its corresponding ureteroscope may render one incompatible with the other. This may lead to additional costs and downtime.

The exemplary features of the present disclosure are directed to improvements in ureteroscopy technology.

SUMMARY

According to aspects of the present disclosure, a medical device may include a tubular member. The medical device may also include a handle assembly connected to the tubular member. The handle assembly may include a handle housing. The handle assembly may also include an illumination assembly. The illumination assembly may include an illumination unit housed within an interior of the handle housing. The illumination assembly may also include an illumination fiber operatively coupled to the illumination unit. The illumination unit may extend through the interior of the handle housing into an interior of the tubular member. The illumination unit may also include a heat sink coupled to the illumination unit. The heat sink may be configured to receive heat from the illumination unit, and dissipate the heat away from the illumination unit.

In addition or alternatively: a surface of the heat sink may be in abutting contact with at least one of an upper surface and a side surface of the illumination unit; the heat sink may surround the illumination unit; a surface of the heat sink may include at least one cavity; at least a portion of the illumination unit may be received within the at least one cavity; the cavity may include a slot extending substantially transverse to a longitudinal axis of the heat sink; the cavity may include a slot extending along a longitudinal axis of the heat sink; the heat sink may include an illumination fiber passageway extending from a first surface of the heat sink to a second surface of the heat sink opposite the first surface; the illumination fiber passageway may receive a proximal portion of the illumination fiber; a surface of the heat sink may include at least one chamfer; the at least one chamfer may include a first chamfer and a second chamfer; the first and second chamfers may be slanted in opposite directions; the at least one chamfer may include a slanted surface facing a concave bend in the illumination fiber; the handle assembly may include a printed-circuit board housed within an interior of the handle housing; at least one of the illumination unit and the heat sink may be mounted on the printed-circuit board; the heat sink may be out of direct contact with the handle housing; the heat sink may be monolithic; the monolithic heat sink may include aluminum; or longest dimensions of the handle housing and the heat sink may extend along the same direction.

According to aspects of the present disclosure, a medical device may include a tubular member. The medical device may also include a handle assembly connected to the tubular member. The handle assembly may include a handle housing. The handle assembly may also include an illumination assembly. The illumination assembly may include a light-emitting diode housed within an interior of the handle housing. The illumination assembly may also include an illumination fiber operatively coupled to the light-emitting diode. The illumination fiber may extend through the interior of the handle housing into an interior of the tubular member. The illumination assembly may also include a heat sink coupled to the light-emitting diode. The heat sink may be configured to receive heat from the light-emitting diode, and dissipate the heat from the light-emitting diode. The heat sink may include a passage through which at least a portion of the illumination fiber extends.

In addition or alternatively, a proximal portion of the illumination fiber may extend through the passage. A proximal end of the illumination fiber may be operatively coupled to the light-emitting diode.

According to aspects of the present disclosure, a method of illuminating with a medical device may include activating an illumination unit housed within an interior of a handle housing. The illumination unit may emit light when activated. The method may also include transmitting the light through the handle housing and into a tubular member coupled to the handle housing. The light may be transmitted through an illumination fiber extending from the illumination unit through the interior of the handle housing and into the tubular member. The method may also include dissipating heat from the illumination unit using a heat sink coupled to the illumination unit, the heat sink being housed within the interior of the handle housing.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview

Embodiments of the present disclosure relate to a medical system for diagnosing and/or treating internal areas of a subject's body. The medical system may include a medical device, a computer and/or display, and an interface box for facilitating communication between the medical device and the computer and/or display.

Exemplary Embodiments

Reference will now be made in detail to exemplary embodiments of the present disclosure described above and illustrated in the accompanying drawings.

The terms "proximal" and "distal" are used herein to refer to the relative positions of the components of an exemplary medical device. When used herein, "proximal" refers to a position relatively closer to the exterior of the body or closer to a user using the medical device. In contrast, "distal" refers to a position relatively further away from the user using the medical device, or closer to the interior of the body.

Figure 1:
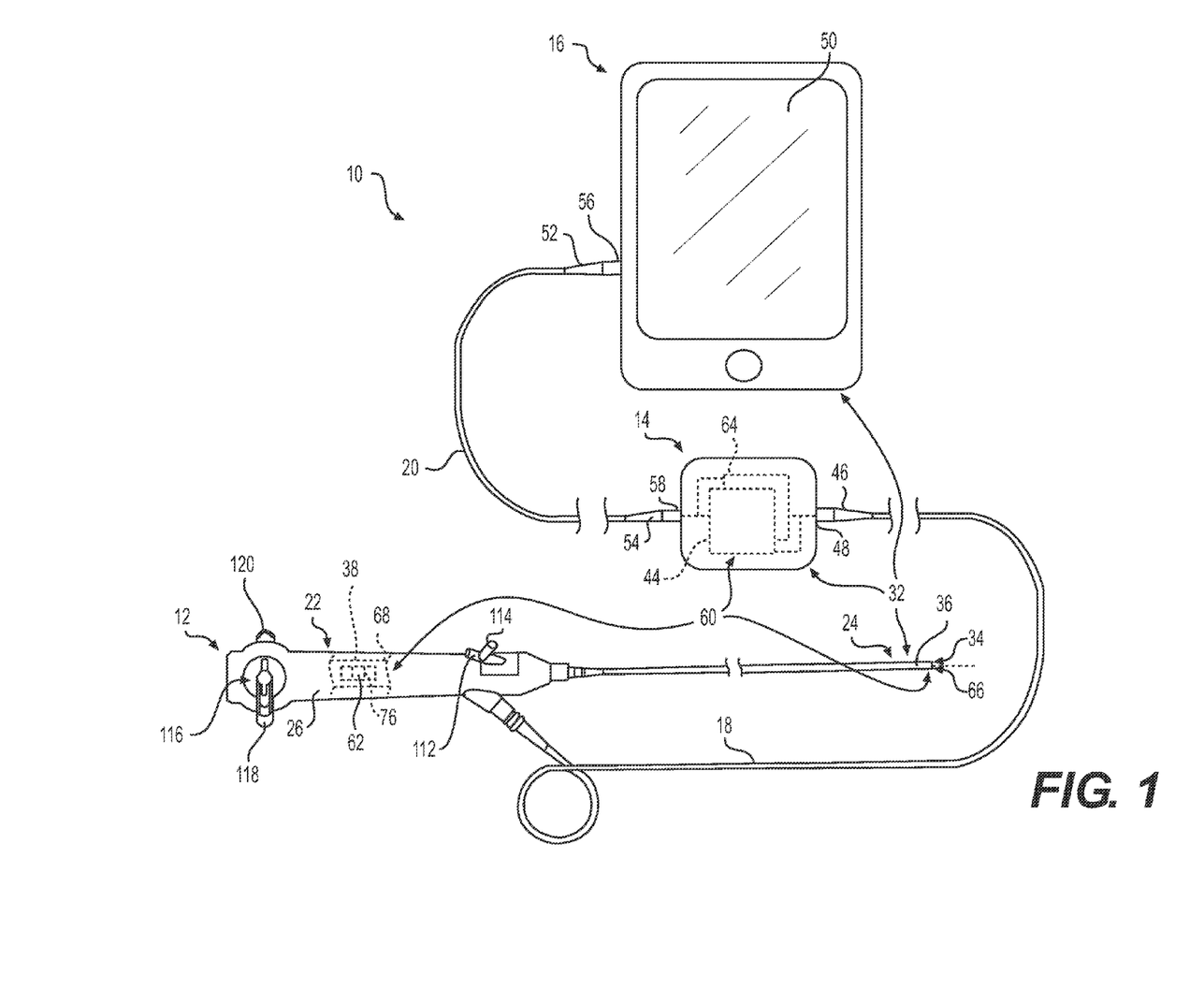
FIG. 1 is an image of an exemplary medical system, in accordance with aspects of the present disclosure.

FIG. 1 shows an exemplary medical system 10. Medical system 10 may include a medical device 12, an interface box 14, and a computer 16. Medical device 12 may be coupled to interface box 14 by a distal connector 18. Computer 16 may be coupled to interface box 14 by a proximal connector 20.

Medical device 12 may include any device configured to allow a user to perform medical diagnoses and/or treatments on a subject. For example, medical device 12 may include any device configured to allow a user to access and view internal areas of a subject's body. Additionally or alternatively, medical device 12 may include any device configured to deliver medical instruments, such as, for example, biopsy forceps, graspers, baskets, snares, probes, scissors, retrieval devices, lasers, and/or other tools, into a subject's body. Medical device 12 may be inserted into a variety of body openings, lumens, and/or cavities. For example, medical device 12 may be inserted into any portion of a urinary tract, such as a ureter, a gastrointestinal lumen, such as an esophagus, a vascular lumen, and/or an airway.

According to aspects of the present disclosure, medical device 12 may be a ureteroscope. In some contemplated embodiments, medical device 12 may be a sterile, single-use, and disposable ureteroscope. Alternatively, medical device 12 may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable.

Medical device 12 may include a handle assembly 22. Medical device 12 may also include an elongate tubular member 24 operably connected to handle assembly 22. Tubular member 24 may include, for example, a catheter, and may be configured to be at least partially inserted into a subject's body and navigated to an internal area therein. Tubular member 24 may be flexible. For example, tubular member 24 may include one or more portions that are flexible. Its flexibility may allow tubular member 24 to be maneuvered into, through, and out of the subject's body. Tubular member 24 may be configured, for example, to traverse tortuous anatomical lumens of the subject's body. Tubular member 24 may be uniformly flexible, or may include a plurality of portions having varying degrees of flexibility or rigidity.

Figure 2:
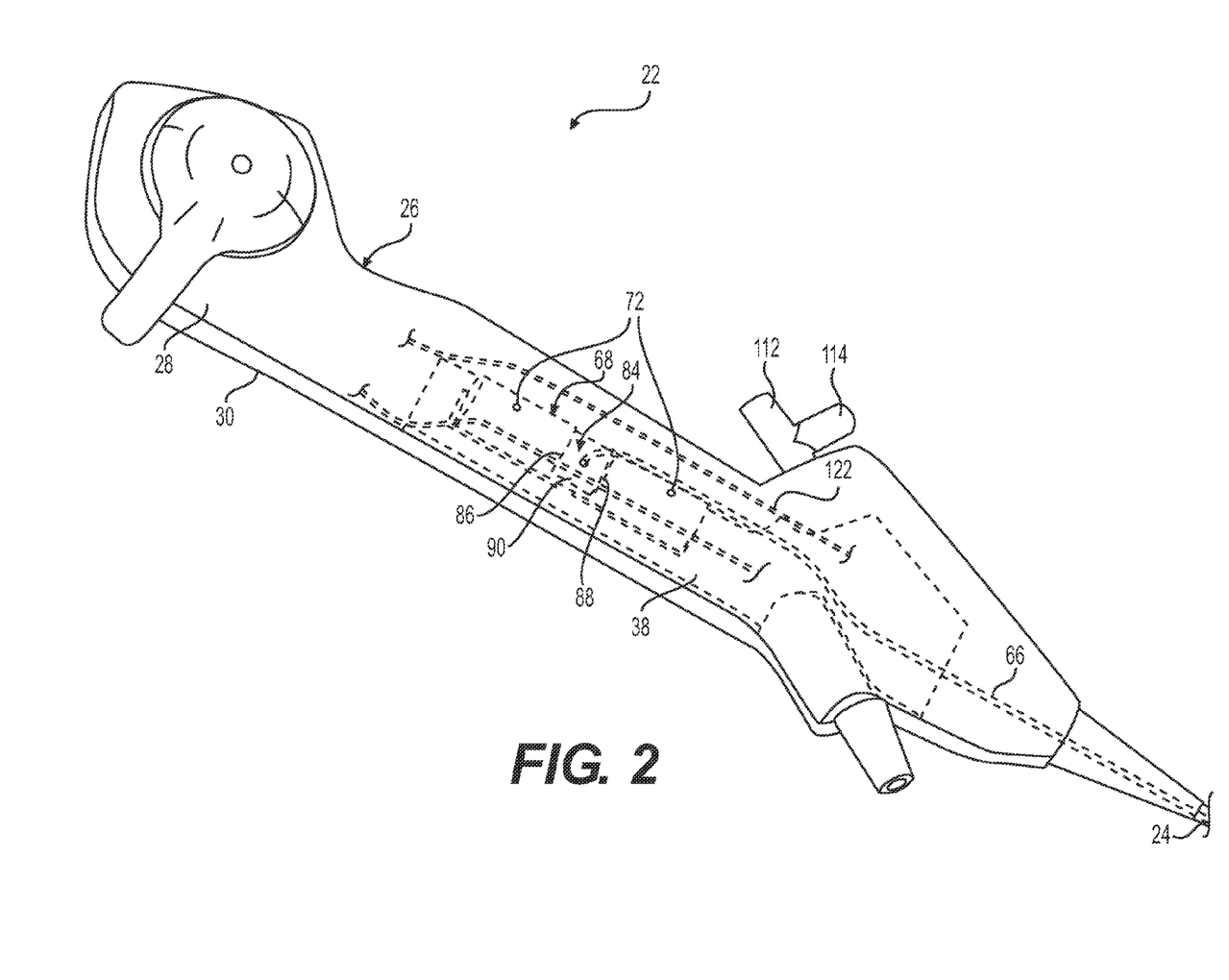
FIG. 2 is a perspective view of an exemplary handle assembly, in accordance with aspects of the present disclosure.

FIG. 2 shows an exemplary embodiment of handle assembly 22. Handle assembly 22 may include a handle housing 26. Handle housing 26 may include two half-portions 28 and 30 joined together by appropriate fasteners. For example, half-portions 28 and 30 may be joined together by removable fasteners, such as screws and pins, or by non-removable fastening techniques, such as heat bonding or adhering with an adhesive.

Medical device 12 may also include an imaging assembly 32. Imaging assembly 32 may include an image sensor 34 at a distal end of tubular member 24. For example, image sensor 34 may be at a distalmost tip of tubular member 24. Image sensor 34 may be at least partially mounted within, or embedded within, the distal end of tubular member 24. It is also contemplated that tubular member 24 may have a distal end cap (not shown), and image sensor 34 may be positioned therein. Image sensor 34 may view an area distal to the distal end of tubular member 24.

Image sensor 34 may be any suitable type of image sensor configured to capture images and/or full-motion video images in digital or any other suitable format. Image sensor 34 may include, for example, a charged couple device ("CCD") or a complementary metal oxide semiconductor ("CMOS") image sensor. Image sensor 34 may include a pixel count greater than 20,000 pixels and less than 70,000 pixels. For example, image sensor 34 may have a pixel count of 62,500. Image sensor 34 may include a field of view of at least 80°.

An image sensor connector 36, which may include, for example, one or more electrical wires or cables extending through an interior of tubular member 24, may connect the image sensor 34 to a printed circuit board ("PCB") 38 mounted within an interior of handle housing 26. PCB 38 may mechanically support and/or electrically connect electronic components using conductive tracks, pads, and other features. PCB 38 may be etched from copper sheets laminated onto a non-conductive substrate. It is contemplated that electronic components like capacitors, resistors, or active devices, may be mounted on PCB 38. A signal amplifier (not shown) is one type of active device that may be mounted on PCB 38. Image data captured by image sensor 34 may be transmitted through image sensor connector 36 to PCB 38. The image data may be amplified by the signal amplifier on PCB 38. A signal converter box (not shown) is another example of an active device that may be mounted on PCB 38.

Figure 5:
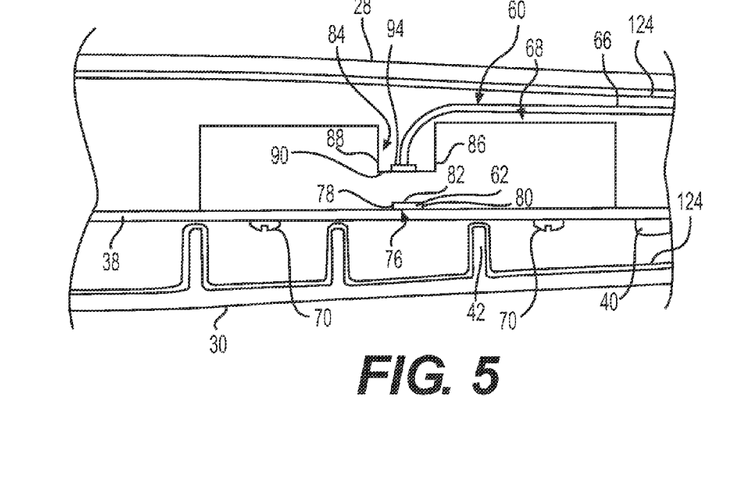
FIG. 5 is a cut-away side view of a portion of a handle assembly, including an interior region of the handle assembly, in accordance with aspects of the present disclosure.

PCB 38 may be secured within handle housing 26 by any suitable attachment. For example, PCB 38 may be fastened by appropriate fasteners 40, such as screws and pins, and/or by fastening techniques, such as heat bonding and adhesive bonding (FIG. 5). PCB 38 may be attached to a suitable ground to discharge errant electrical surges, so such surges are less likely to damage components in electronic communication with PCB 38. It is also contemplated that PCB 38 may be supported in handle housing 26 by one or more structures 42, such as ridges or protrusions, extending toward PCB 38 from an interior surface of handle housing 26.

Imaging assembly 32 may also include an imaging card or circuit board 44, shown in FIG. 1. Imaging card 44 may be housed in interface box 14. Imaging card 44 may include, for example, any suitable circuit board configured to drive the capture of image data with image sensor 34. For example, imaging card 44 may include appropriate circuitry and memory to calibrate captured image data from image sensor 34, deserialize the captured image data, perform known algorithms, such as demosaicing, gain control, and white balance, and/or any other suitable functions, to produce a quality color image. The gain control may be implemented by imaging card 44 by adjusting gains applied to the image data from image sensor 34.

Alternatively, imaging card 44 may include appropriate circuitry and memory to calibrate captured image data from image sensor 34, decode or deserialize the captured image data, and format the data for transmission to computer 16. Computer 16 may perform known algorithms, such as demosaicing, gain control, and white balance, and/or any other suitable functions, to produce a quality color image. The gain control may be implemented by computer 16 by adjusting gains applied to the image data from image sensor 34.

Imaging card 44 may also include isolation circuitry to prevent undesired radio frequency susceptibility, emissions and interference, as well as undesired leakage currents in the event of an electrical failure. Interface box 14 and imaging card 44 may be coupled to handle assembly 22 and PCB 38 by distal connector 18. Imaging card 44 may receive image data from image sensor 34 through image sensor connector 36, PCB 38, and distal connector 18.

Distal connector 18 may operably connect handle assembly 22 to interface box 14. Distal connector 18 may provide an electronic signal pathway for signals between interface box 14 and imaging assembly 32. For example, distal connector 18 may provide a communication pathway for signals between imaging card 44 and PCB 38. Distal connector 18 may also provide power from interface box 14 to medical device 12. Distal connector 18 may include a scope cable. The scope cable may include one or more electrical wires, and/or an electrical conduit. Distal connector 18 may also include a suitable structure on its proximal end, such as a proximal plug 46, configured to readily attach to and detach from interface box 14, by entering into and exiting from a distal port 48 of interface box 14. For example, proximal plug 46 may include a point-to-point adapter, splice, multi-port adapter, and/or a snap-fit connection. Distal connector 18 may also include a distal plug (not shown), configured to readily attached to and detach from a proximal port (not shown) on medical device 12. Accordingly, distal connector 18 may operably link medical device 12 to interface box 14 when performing a procedure utilizing medical device 12. Distal connector 18 may readily detach medical device 12 from interface box 14 when the procedure is completed, and medical device 12 is to be disposed of, or sterilized for subsequent use. It is also contemplated that in some embodiments, distal connector 18 may be fixedly attached to at least one of interface box 14 and medical device 12.

Imaging assembly 32 may also include one or more components forming computer 16. Computer 16 may include a smartphone, tablet computer, laptop computer, desktop computer, and/or any other suitable computing device. Computer 16 may include a display 50, as well as other electronic components (not shown), such as a central processing unit, memory, video and graphics cards, wireless and wired networking devices, audio devices, one or more input/output ports, a power supply, and/or any other suitable computer features. Computer 16 may include rear side VESA compatible mounting holes (not shown) by which interface box 14 may be mounted to computer 16. In other embodiments, computer 16 may be replaced by a screen or monitor with less of, or without, the computing power of computer 16.

In one embodiment, display 50 may include a touch screen for displaying image data, and for receiving inputs or commands from a user. User interaction may be directed toward aspects of image capture, video capture, brightness control, mode controls, narrow band imaging toggle, and/or any other controls that may be part of a typical ureteroscopy procedure. Display 50 may be mounted on a structure (not shown), such as an existing tower using an adjustable arm, a subject bed, a boom system, on a monitor mount on a stand, and/or on a separate rolling or stationary stand.

Computer 16 may be coupled to interface box 14, and imaging card 44, by proximal connector 20. Computer 16 may receive image data from imaging card 44 via proximal connector 20. Computer 16 may include imaging electronics configured to process and/or transfer the image data, display the image data on display 50 for viewing by a user, and send signals to imaging card 44 for controlling electronic components of PCB 38 and/or image sensor 34. For example, imaging card 44 may calibrate captured image data based on commands from computer 16.

Proximal connector 20 may operably connect interface box 14 to computer 16. Proximal connector 20 may provide an electronic signal pathway for signals between computer 16 and interface box 14. For example, proximal connector 20 may provide a communication pathway for signals between computer 16 and imaging card 44. Proximal connector 20 may also provide power from a power supply, such as a battery or power adapter of computer 16, to imaging card 44. Proximal connector 20 may be a cable, such as a universal serial bus ("USB") cable, and may include, for example, one or more electrical wires, and/or an electrical conduit. Proximal connector 20 may also include a suitable structure on each end, such as a proximal plug 52 and a distal plug 54. The proximal plug 52 may be configured to readily attach to and detach from computer 16, by entering and exiting from a port 56 of computer 16. The distal plug 54 may be configured to readily attach to and detach from interface box 14, by entering and exiting from a proximal port 58 of interface box 14. For example, proximal and distal plugs 52 and 54 may include point-to-point adapters, splices, multi-port adapters, snap-fit connections, and/or USB plugs. Accordingly, proximal connector 20 may operably link computer 16 to interface box 14 when performing a procedure, and may readily detach from interface box 14 and/or computer 16 when the procedure is completed.

The ease of attaching and detaching computer 16, interface box 14, and medical device 12, with proximal and distal connectors 18 and 20, may provide a user with the ability to easily switch out any one of, or any combination of components. This may be beneficial when, for example, one or more of the components malfunctions. The malfunctioning components may be unplugged, and replaced with functioning components. Furthermore, it is contemplated that multiple types of medical devices may be used with a single computer by, for example, plugging in an appropriate interface box to ensure compatibility between the computer and whatever medical device is being used. When the medical device is switched for another, a different interface box may be connected between the computer and the medical device. Another potential benefit is that if the computer and/or the medical device is upgraded, the interface box can be modified to ensure continued compatibility between the two components.

Medical device 12 may also include an illumination assembly 60. As shown in FIGS. 1 and 5, illumination assembly 60 may include an illumination unit 62, such as a light-emitting diode ("LED"), an illumination card or circuit board 64, at least one illumination fiber 66, and a heat sink 68. LED 62 may be mounted on PCB 38 in the interior of handle housing 26. Exemplary embodiments are shown in FIGS. 1, 2, and 5. LED 62 may be mounted on conductive tracks or pads on PCB 38. LED 62 may emit light upon receipt of an appropriate power supply. The power supply may come from computer 16, for example from a batter or power adapter of computer 16, via connectors 18 and 20 and interface box 14. LED 62 may include, for example, a LUXEON Z LED. Any other suitable LED may be used.

Illumination fiber 66, shown in FIGS. 2 and 5, may be coupled at a proximal end to LED 62, and at a distal end to the distal end of tubular member 24. Illumination fiber 66 may transmit the light emitted by LED 62 to the distal end of tubular member 24, where the light may be emitted from the distal tip of illumination fiber 66 to areas around the distal end of tubular member 24. Illumination fiber 66 may include an optical fiber made of plastic, glass, or any other suitable light transmissive material.

Illumination card 64 may be housed in interface box 14, as shown in FIG. 1. Illumination card 64 may help drive and/or control operation of LED 62. For example, illumination card 64 may help control the light output of LED 62. Distal connector 18 may provide electronic signaling pathways for illumination card 64 to control light output from LED 62. The electronic signaling pathways may be similar to the ones linking imaging card 44 to PCB 38. Distal connector 18 may also provide an electrical conduit for power to be supplied to LED 62 from illumination card 64. Proximal connector 20 may provide a communication pathway for signals between computer 16 and illumination card 64. Proximal connector 20 may also provide power from the power supply of computer 16 to illumination card 64, for use by LED 62.

Because LED 62 is in handle housing 26, and not, for example, in interface box 14 or computer 16, illumination fibers may be omitted from proximal and distal connectors 18 and 20. Thus, specialized connectors with illumination fibers therein are not required for medical system 10. For example, conventional USB and scope cables may be used. Further, because LED 62 is in handle housing 26 rather than in computer 16, computers that do not include LEDs therein may be used in medical system 10. Furthermore, because LED 62 is not, for example, at the distal end of tubular member 24, the diameter of the distal end need not be enlarged to fit LED 62 and any heat sinks necessary to cool LED 62.

It is contemplated that one or more actuators or buttons (not shown) may be disposed on handle assembly 12, for controlling operation of LED 62. Additionally or alternatively, one or more actuators or buttons may be disposed on computer 16, for controlling operation of LED 62. In one embodiment, gain control for imaging may be implemented by adjusting the intensity of LED 62, and adjusting the gains applied to the signals by image sensor 34. That gain control may be implemented by computer 16, imaging card 44 and illumination card 64, and/or electronic components on PCB 38.

LED 62 may generate heat when activated. The heat may be dissipated from LED 62 by heat sink 68. Heat sink 68 may be mounted on PCB 38. Heat sink 68 may be mounted using any suitable attachment. For example, heat sink 68 may be fastened to PCB 38 by appropriate fasteners 70, such as screws and pins, and/or by fastening techniques, such as heat bonding and adhesive bonding. When mounted on PCB 38, a bottom surface of heat sink 68 may contact one or more surfaces of LED 62. Heat generated by LED 62 may transfer into heat sink 68, and heat sink 68 may dissipate the heat.

Heat sink 68 may remain out of contact with handle housing 26, as shown in FIG. 5. This may ensure that heat dissipated from heat sink 68 may not directly heat a portion of handle housing 26, thereby possibly damaging handle housing 26 or making it uncomfortable for a user to grip handle housing 26.

Figure 3:
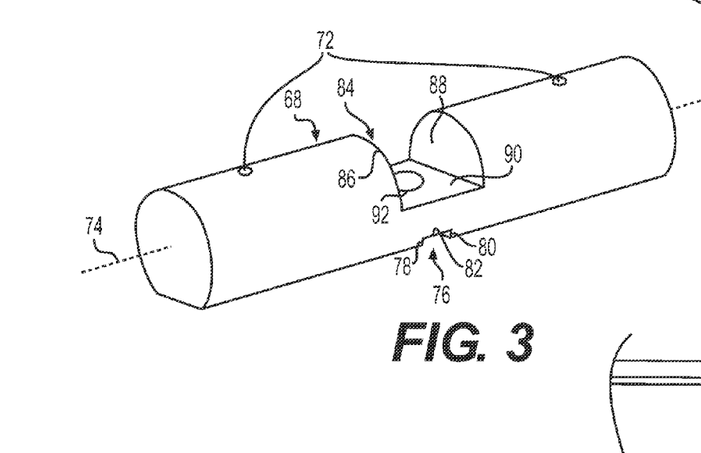
FIG. 3 is a perspective view of an exemplary heat sink, in accordance with aspects of the present disclosure.
Figure 4:
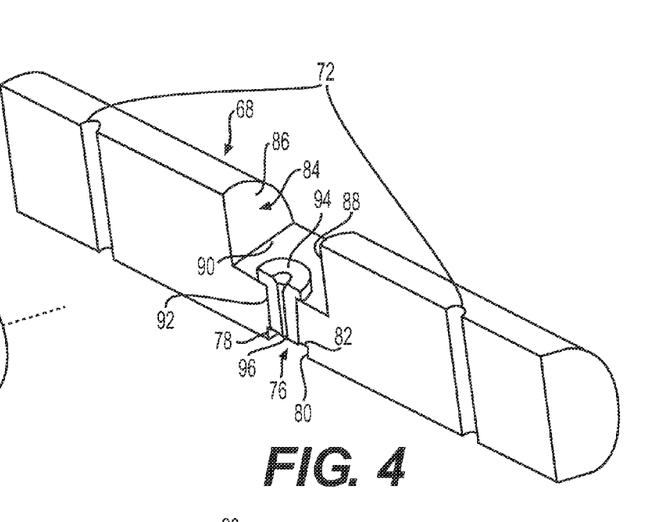
FIG. 4 is a perspective cross-sectional view of the exemplary heat sink of FIG. 3, in accordance with aspects of the present disclosure.

Heat sink 68 may include one or more mounting holes 72 for receiving fasteners 70 to fasten heat sink 68 to PCB 38. Mounting holes 72 may extend in a direction substantially transverse to a longitudinal axis 74 of heat sink 68. Heat sink 68 may include a lower cavity 76 on its bottom surface. Lower cavity 76 may include, for example, a slot, groove, or channel. Lower cavity 76 may have at least three side surfaces 78, 80, and 82. Lower cavity 76 may have two open ends. Lower cavity 76 may extend in a direction substantially transverse to longitudinal axis 74. For example, the direction lower cavity 76 extends from one open end to another open end, may be substantially perpendicular to longitudinal axis 74.

LED 62 may be at least partially received in lower cavity 76. It is contemplated that lower cavity 76 may have a shape substantially complementary to the shape of LED 62, for a close fit of LED 62 in lower cavity 76. Portions of the bottom surface of heat sink 68 that form lower cavity 76 may be in close abutting contact with portions of LED 62. For example, surfaces 78, 80, may be in close abutting contact with top and side surfaces of LED 62. In another embodiment, lower cavity 76 may have closed ends, rather than open ends. In such an embodiment, surfaces 78, 80, and 82, and the surfaces forming the closed ends, may surround LED 62. Those surfaces may also be in close and/or abutting contact with surfaces of LED 62.

It is also contemplated that a layer of material may be provided between surfaces of heat sink 68 and LED 62 prevent one from damaging the other by rubbing or impact, and/or to ensure close contact between heat sink 68 and LED 62, while still allowing heat to be transmitted from LED 62 to heat sink 68 through the layer of material. For example, the layer of material may include thermal adhesive or thermal grease.

Heat sink 68 may also include an upper cavity 84 on its top surface. Upper cavity 84 may include a slot, groove, or channel. Upper cavity 84 may have at least three side surfaces 86, 88, and 90. Upper cavity 84 may have two open ends. Upper cavity 84 may extend in a direction substantially transverse to longitudinal axis 74. For example, the direction upper cavity 84 extends from one open end to the other open end, may be substantially perpendicular to longitudinal axis 74. Upper and lower cavities 76 and 84 may extend in the same direction. Portions of upper and lower cavities 76 and 84 may overlap.

An illumination fiber passageway 92 may connect upper cavity 84 to lower cavity 76. Illumination fiber passageway 92 may extend in a direction substantially transverse to longitudinal axis 74. Illumination fiber passageway 92 may extend from surface 90 of upper cavity 84 to surface 82 of lower cavity 76. A proximal portion of illumination fiber 66 may extend through illumination fiber passageway 92. The proximal portion of illumination fiber 66 may be press fit into, adhered to, and/or otherwise coupled to illumination fiber passageway 92. Alternatively, a ferrule 94 may be inserted into illumination fiber passageway 92. Ferrule 94 may be press fit into, adhered to, and/or otherwise coupled to illumination fiber passageway 92. Ferrule 94 may include its own illumination fiber passageway 96, into which illumination fiber 66 may be inserted. Ferrule 94 may help protect illumination fiber 66 from being damaged by being forced against heat sink 68, or by being excessively heated by heat in heat sink 68. The proximal portion of illumination fiber 66 may be press fit into, adhered to, and/or otherwise coupled to illumination fiber passageway 96.

The illumination fiber 66 may extend out of illumination fiber passageway 92 and/or 96. A portion of illumination fiber 66 may bend toward the direction of tubular member 24. The bending may occur above heat sink 68. A width of upper cavity 84 may be greater than a width of lower cavity 76, to provide a clearance between illumination fiber 66 and heat sink 68 as illumination fiber 66 bends. The clearance may reduce the risk of damaging illumination fiber 66 through inadvertent contact between it and the upper surfaces and/or edges of heat sink 68. The width of lower cavity 76 may be less than the width of upper cavity 84 to provide close contact between bottom surfaces of heat sink 68 and surfaces of LED 62.

Figure 6:
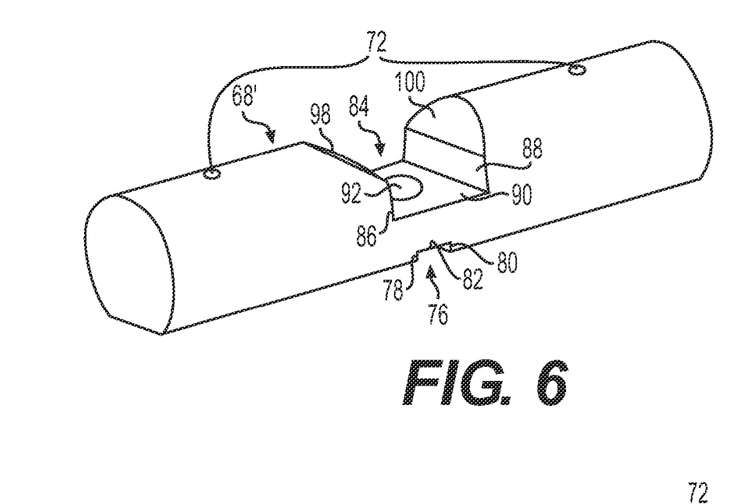
FIG. 6 is a perspective view of an exemplary heat sink, in accordance with aspects of the present disclosure.

An exemplary heat sink 68' may include a chamfer 98 and/or a chamfer 100 (FIG. 6) to provide additional clearance between illumination fiber 66 and the upper surfaces and edges of heat sink 68'. Chamfers 98 and 100 may be on opposite halves of heat sink 68'. Chamfers 98 and 100 may include surfaces slanted in opposing directions. Chamfers 98 and 100 may extend from upper edges of surfaces 86 and 88 of upper cavity 84. Chamfer 98 may be angled relative to surface 86. Opposing chamfer 100 may be angled relative to opposing surface 88. Any suitable angle is contemplated. For example, an angle of between approximately 5 and 85 degrees may be used. It is contemplated that the angle may be around 45 degrees for some embodiments. Chamfers 98 and 100 may provide clearance while leaving heat sink 68' with material in other regions to help with heat dissipation. In one embodiment, only one of chamfers 98 and 100 may be provided to create clearance for illumination fiber 66, depending on the path of illumination fiber 66 over heat sink 68'. In another embodiment, both chamfers 98 and 100 may be provided to ensure that the additional clearance may be provided regardless of the orientation in which heat sink 68' is mounted on PCB 38, or the direction in which illumination fiber 66 is bent over the upper surface of heat sink 68'. A concave portion of the bend in illumination fiber 66 may face the slanted surface formed by one of chamfers 98 and 100. Heat sink 68' may be formed by removing material from heat sink 68, to form chamfers 98 and 100.

Figure 8:
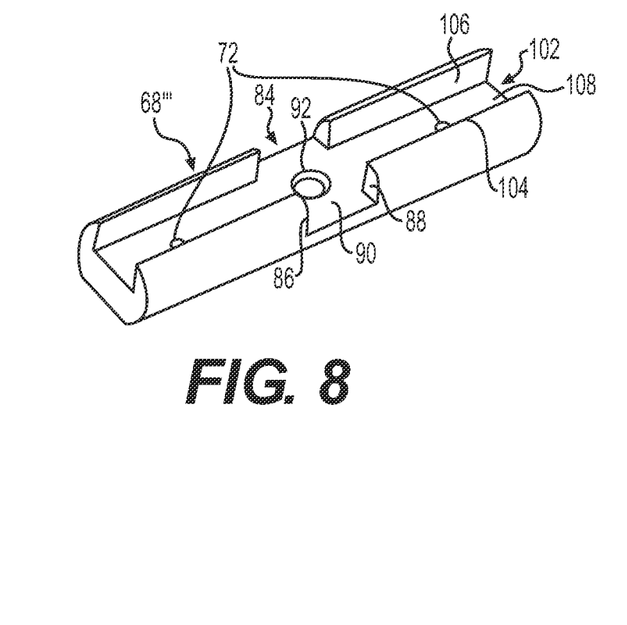
FIG. 8 is a perspective view of a heat sink, in accordance with aspects of the present disclosure.

An exemplary heat sink 68''' may include an upper cavity 102 on its top surface (FIG. 8). Upper cavity 102 may include, for example, a slot, groove, or channel. Upper cavity 102 may have three surfaces 104, 106, and 108. Upper cavity 102 may have two open ends. Upper cavity 102 may extend in a direction substantially in line with or parallel to longitudinal axis 74. For example, the direction upper cavity 102 extends from one open end to another open end, may be in line with or parallel to longitudinal axis 74. The open ends of upper cavity 102 may be positioned at proximalmost and distalmost ends of heat sink 68'''. Upper cavity 102 may extend in a direction substantially transverse to the direction in which upper cavity 84 and/or lower cavity 76 extend. When illumination fiber 66 extends over heat sink 68''' in a direction along longitudinal axis 74, upper cavity 102 may provide additional clearance between upper surfaces and edges of heat sink 68 and illumination fiber 66. It is contemplated that illumination fiber 66 may extend within the space created by upper cavity 102, to reduce the vertical profile of the combined assembly of heat sink 68''', illumination fiber 66, and LED 62.

Figure 7:
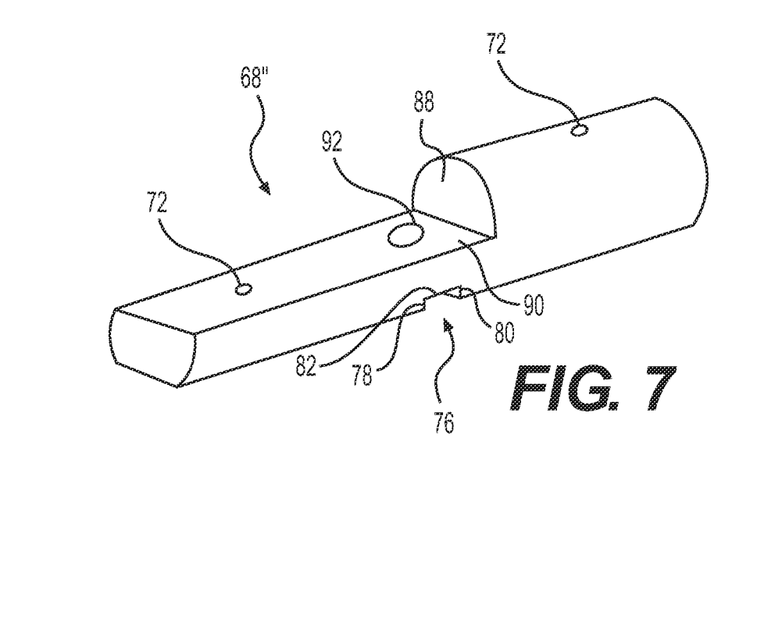
FIG. 7 is a perspective view of a heat sink, in accordance with aspects of the present disclosure.

Additionally or alternatively, an exemplary heat sink 68'' may include a portion forming a substantially flat plate, as shown in FIG. 7, to provide additional clearance for illumination fiber 66. It is contemplated that one or more of heat sinks 68'' and 68''' may be formed by removing material from heat sink 68.

Heat sinks 68, 68', 68'', and 68''' may be desirable for their compactness in a dimension transverse to longitudinal axis 74. The length of heat sinks 68, 68', 68'', and 68''' along longitudinal axis 74 may also be desirable for distributing heat over a longer portion of the interior of handle housing 26. This may reduce the likelihood of hot spots developing in regions of handle housing 26. It is contemplated that interior surfaces of handle housing 26 may be coated with a material 124, such as a metallic material, to help distribute the heat more evenly along the length of handle housing 26 (FIG. 5).

The extent of heat sinks 68, 68', 68'', and 68''' along longitudinal axis 74, and the compactness of heat sinks 68, 68', 68'', and 68''' along a transverse direction, may also be desirable for matching the elongate shape of handle housing 26. The length of handle housing 26 may be greater than the width of handle housing 26. Since heat sinks 68, 68', 68'', and 68''' may also be longer that they are wide, heat sinks 68, 68', 68'', and 68''' may make use of the longest dimension (the length) of handle housing 26, while creating less of an obstacle along the shorter dimension (the width) of handle housing 26.

One or more of heat sinks 68, 68', 68'', and 68''' may be monolithic. For example, one or more of heat sinks 68, 68', 68'', and 68''' may be formed from a substantially cylindrical metallic blank or rod. For example, the blank or rod may be made of aluminum or an alloy thereof, or any other suitable metal or metal alloy. The ends of the blank may be cut to a desired length to fit the interior of handle housing 26. A curved surface of the blank may be machined to form a substantially flat longitudinally-extending strip. The strip may be the bottom or lower surfaces of heat sinks 68, 68', 68", and 68'". The flatness of the strip may provide a stable surface for mounting heat sinks 68, 68', 68", and 68'" on PCB 38, which may have a substantially flat upper surface. By ensuring that heat sinks 68, 68', 68", and 68'" are mounted on PCB 38 in a firm and stable manner, contact between heat sinks 68, 68', 68", and 68'" and LED 62, which may be mounted on PCB 38, may be maintained.

Cavities 76, 84, and 102, chamfers 98 and 100, plate 110, mounting holes 72, and/or illumination fiber passageway 92, may be formed by machining portions of the blank. Machining may include, for example, milling, grinding, drilling, and/or any other suitable material removal processes. Alternatively, it is contemplated that heat sink 68 may be molded to have one or more of the aforementioned structures. With molding, performance of material removal processes may not be required.

Handle assembly 22 may also include ports 112 and 114. Ports 112 and 114 may provide access to one or more channels (not shown) extending through tubular member 24. For example, port 112 and/or port 114 may provide access for one or more medical instruments into one or more channels extending through tubular member 24 and out the distal tip of tubular member 24. Additionally or alternatively, port 112 and/or port 114 may provide access into one or more working channels for delivering a suitable fluid, such as a liquid or gas, for irrigation and insufflation purposes, respectively, to and out of the distal tip of tubular member 24. It is also contemplated that port 112 and/or port 114 may be in fluid communication with one or more working channels for withdrawing material from tubular member 24 and/or an area near the distal tip of tubular member 24, using suction. Tubular member 24 may include one or more additional channels for receiving other components, such as image sensor connector 36, and/or illumination fiber 66.

Handle assembly 22 may also include a steering mechanism 116 (FIGS. 1 and 2). Steering mechanism 116 may be configured to control the steering and deflection of tubular member 24. Steering mechanism 116 may include a first actuator 118 and a second actuator 120 configured to control deflection of a distal portion of tubular member 24 between a substantially linear configuration and a variety of curved, angled, or bent configurations, in a variety of different directions relative to a longitudinal axis 74 of tubular member 24. For example, actuating first actuator 118 in opposing directions may cause the distal portion of tubular member 24 to deflect in opposing directions along a first plane. Actuating second actuator 120 in opposing directions may cause the distal portion of tubular member 24 to deflect in opposing directions along a second plane different than the first plane. Accordingly, steering mechanism 116 may provide four-way steering of the distal portion of tubular member 24. The ability to steer allows the user to achieve visualization of almost any internal area in the subject's body.

Steering mechanism 116 may include one or more control members including, for example, one or more control members 122. Control members 122 may be coupled to first and second actuators 118 and 120, and may extend through handle housing 26 and through tubular member 24. Furthermore, control members 122 may each be coupled to tubular member 24 at or near the distal tip of tubular member 24. Control members 122 may be supported by portions of handle housing 26, such that portions of control members 122 are curved away from or otherwise spaced from heat sink 68. First and second actuators 118 and 120 may control deflection of a distal portion of tubular member 24 by selectively extending and retracting control members 122. Control members 122 may include four Bowden cables. One pair of cables may be selectively pushed and pulled by moving first actuator 118 proximally and distally to deflect the distal portion of tubular member 24 in two directions along a first plane. The other pair of cables may be selectively pushed and pulled by moving second actuator 120 proximally and distally to deflect the distal portion of tubular member 24 in two directions along a second plane transverse to the first plane.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

We claim:
1. A medical device comprising:
   a tubular member;
   a handle assembly connected to the tubular member, the handle assembly including:
      a handle housing, and
      an illumination assembly including:
         an illumination unit housed within an interior of the handle housing,
         an illumination fiber operatively coupled to the illumination unit, the illumination fiber extending through the interior of the handle housing into an interior of the tubular member, and
         a heat sink coupled to the illumination unit, the heat sink being configured to receive heat from the illumination unit, and dissipate the heat away from the illumination unit, at least one surface of the heat sink being in abutting contact with a light-emitting diode of the illumination unit,
   wherein a surface of the heat sink includes at least one chamfer that includes a slanted surface facing a concave bend in the illumination fiber.

2. The medical device of claim 1, wherein the heat sink surrounds the illumination unit.

3. The medical device of claim 1, wherein a surface of the heat sink includes at least one cavity, and at least a portion of the illumination unit is received within the at least one cavity.

4. The medical device of claim 3, wherein the cavity includes a slot extending substantially transverse to a longitudinal axis of the heat sink.

5. The medical device of claim 3, wherein the cavity includes a slot extending along a longitudinal axis of the heat sink.

6. The medical device of claim 1, wherein the heat sink includes an illumination fiber passageway extending from a first surface of the heat sink to a second surface of the heat sink opposite the first surface, the illumination fiber passageway receiving a proximal portion of the illumination fiber.

7. The medical device of claim 1, wherein the at least one chamfer includes a first chamfer and a second chamfer.

8. The medical device of claim 7, wherein the first and second chamfers are slanted in opposite directions.

9. The medical device of claim 1, wherein the handle assembly includes a printed-circuit board housed within an interior of the handle housing.

10. The medical device of claim 9, wherein at least one of the illumination unit and the heat sink is mounted on the printed-circuit board.

11. The medical device of claim 1, wherein the heat sink is out of direct contact with the handle housing.

12. The medical device of claim 1, wherein the heat sink is monolithic.

13. The medical device of claim 12, wherein the monolithic heat sink includes aluminum.

14. The medical device of claim 1, wherein longest dimensions of the handle housing and the heat sink extend along the same direction.

15. A medical device comprising:
a tubular member;
a handle assembly connected to the tubular member, the handle assembly including:
a handle housing, and
an illumination assembly including:
a light-emitting diode housed within an interior of the handle housing,
an illumination fiber operatively coupled to the light-emitting diode and extending through the interior of the handle housing into an interior of the tubular member, and
a heat sink including:
at least one surface in abutting contact with the light-emitting diode, the at least one surface being configured to receive heat from the light-emitting diode, and dissipate the heat from the light-emitting diode, and
a passage through which at least a portion of the illumination fiber extends,
wherein a surface of the heat sink includes at least one chamfer that includes a slanted surface facing a concave bend in the illumination fiber.

16. The medical device of claim 15, wherein a proximal portion of the illumination fiber extends through the passage, and a proximal end of the illumination fiber is operatively coupled to the light-emitting diode.

17. A method of illuminating with a medical device, the method comprising:
activating an illumination unit housed within an interior of a handle housing, the illumination unit having a light-emitting diode configured to emit light when the unit is activated;
transmitting the light through the handle housing and into a tubular member coupled to the handle housing, the light being transmitted through an illumination fiber extending from the illumination unit through the interior of the handle housing and into the tubular member; and
dissipating heat from the illumination unit using a heat sink coupled to the illumination unit, the heat sink being housed within the interior of the handle housing, and having at least one surface in abutting contact with the light-emitting diode,
wherein a surface of the heat sink includes at least one chamfer that includes a slanted surface facing a concave bend in the illumination fiber.

18. The medical device of claim 1, wherein a material is disposed between the light-emitting diode and the at least one surface.

* * * * *